United States Patent [19]
Cullo et al.

[11] Patent Number: 4,814,531
[45] Date of Patent: Mar. 21, 1989

[54] SILICA-TITANIA HYDROCARBON CONVERSION CATALYST

[75] Inventors: Leonard A. Cullo, Greensburg; Francis J. Shiring, III, Hampton Township, Allegheny County, both of Pa.

[73] Assignee: Aristech Chemical Corporation, Pittsburgh, Pa.

[21] Appl. No.: 78,448

[22] Filed: Jul. 27, 1987

Related U.S. Application Data

[63] Continuation-in-part of Ser. No. 923,502, Oct. 27, 1986, which is a continuation-in-part of Ser. No. 796,136, Nov. 8, 1985, Pat. No. 4,711,869.

[30] Foreign Application Priority Data

Sep. 30, 1986 [CA] Canada ................................. 519419
Oct. 31, 1986 [JP] Japan ................................. 61-258695

[51] Int. Cl.$^4$ ............................. C07C 2/66; C07C 2/64
[52] U.S. Cl. ..................................... 585/467; 585/446; 568/804
[58] Field of Search ................. 568/804; 585/446, 467

[56] References Cited

U.S. PATENT DOCUMENTS

| | | | |
|---|---|---|---|
| 1,908,190 | 5/1933 | Schollkopf | 585/446 |
| 2,115,884 | 5/1938 | Schollkopf | 585/446 |
| 2,881,227 | 4/1959 | Keizer | 585/446 |
| 3,636,182 | 1/1972 | Kallos | 585/446 |

FOREIGN PATENT DOCUMENTS

| | | | |
|---|---|---|---|
| 737012 | 6/1966 | Canada | 585/446 |
| 0104607 | 4/1984 | European Pat. Off. | 585/446 |
| 0001140 | 1/1985 | Japan | 585/446 |
| 2029536 | 2/1987 | Japan | 585/446 |

Primary Examiner—Werren B. Lone
Attorney, Agent, or Firm—William L. Krayer

[57] ABSTRACT

Crystalline silica-titania catalyst compositions, optionally containing magnesium, are disclosed; the titanium is introduced through the use of organo-titanate chelates wherein the titanium has a coordination number of at least 5. The compositions are used in acid-catalyzed reactions such as alkylation reactions.

4 Claims, No Drawings

SILICA-TITANIA HYDROCARBON CONVERSION CATALYST

This application is a continuation-in-part of co-pending application U.S. Ser. No. 923,502, filed Oct. 27, 1986, which is a continuation-in-part of U.S. Ser. No. 796,136, filed Nov. 8, 1985, now U.S. Pat. No. 4,711,869 both of which are incorporated herein.

TECHNICAL FIELD

This invention relates to crystalline silica-titania composite zeolite materials, optionally containing magnesium also in the crystalline structure, and their use as catalysts in hydrocarbon conversion reactions requiring acidic conditions for catalysis. The materials also exhibit shape-selective catalytic behavior as a function of their regular, fine pore structure. In general, molecules with effective kinetic diameters of less than 7-8 angstroms will have ready access to the internal catalytic sites and molecules having greater effective kinetic diameters will be excluded. Our catalyst material may contain up to about 10.0% magnesium as MgO.

Such catalysts represent significant advantages over prior art catalysts for acid catalyzed reactions, particularly those involving substituted or unsubstituted monoaromatic molecules. Reactions such as alkylation, dehydration, isomerization, disproportionation and cracking can be effectively catalyzed. Our new material is also proposed as a support for other catalytic materials having catalytic functions, such as vanadium and noble metals, where the beneficial strong-metal support-interaction properties of titania are realized.

Prior to the present invention, the use of titanium in hyrocarbon conversion catalysts has been most commonly proposed only as an adjunct to a pre-formed silicalite or pre-formed silica-alumina catalyst such as those of the ZSM series. See U.S. Pat. No. 4,358,397 as an example. The distribution of titanium-containing compounds on the structure of a pre-formed crystalline material, such as in U.S. Pat. No. 4,358,397, typically involves minimal, if any, chemical reaction of the titanium with the crystal lattice of the catalyst, the manufacturing technique usually comprising primarily a physical distribution of discrete moieties of the titanium compound throughout the labyrinthine structure in a more or less uneven manner.

More recently, Taramasso et al, in U.S. Pat. No. 4,410,501, have disclosed a crystalline material comprising silicon oxide and titanium oxide; it is, however, made using only rapidly hydrolyzable titanium compounds and primarily for this reason has a crystal structure different from ours, as explained further herein. The European patent application No. 84106366.2 filed June 4, 1984 by Norton Company for Saleh employs soluble hydrated titanates, specifically $NaTiO_3H$, with a silica sol for autoclaving, said to produce a crystalline molecular sieve of silicon, titanium, and oxygen. See also U.S. Pat. No. 4,396,783, disclosing a "titanium silicalite" prepared with the use of tetraethyltitanate, and suggesting other rapidly hydrolyzable titanium compounds.

Our invention differs from these specifications, inter alia, in that we employ hydrolysis-resistant chelates of titanium-bearing compounds, wherein the titanium has a coordination number of at least 5, giving rise to a unique distribution of titanium in the dried and calcined product.

The reader may also be interested in reviewing U.S. Pat. No. 4,500,651 suggesting broadly the use of "titanium chelates" to make certain phosphorous and aluminum-containing molecular sieves and employing specifically titanium acetylacetonate.

DISCLOSURE OF INVENTION

We have invented certain new crystalline catalysts containing silicon, titanium, and, optionally, magnesium; methods of making them, and methods of performing certain hydrocarbon conversion reactions with them.

Expressed in terms of moles of oxides, our new compositions comprise 0.015 to 0.040 $TiO_2$:1 $SiO_2$ together with up to 0.17 mole MgO. As has become known in the art, it is extremely difficult to completely exclude alumina and, although we prefer lesser amounts, we can tolerate up to about 1000 or more ppm $Al_2O_3$ in our composite.

In the method of preparation of our composition, a titanium-containing organo-metallic compound resistant to hydrolysis is added directly to the catalyst synthate, rather than impregnating or depositing a titanium-containing compound on a silica rich substrate as in certain prior art processes such as those described in U.S. Pat. No. 4,358,397.

Most titanium salts and organic titanium compounds are subject to hydrolysis upon exposure to water or moist air. These compounds are not useful in the preparation of the catalyst of this invention. However, the triethanolamine chelate, acetylacetonate chelate and the ammonium salts of the lactic acid chelates are more resistant to hydrolysis. This enables them to be added to the aqueous synthesis mixture of the catalyst of this invention, and under hydrothermal conditions the mixture will yield a crystalline material with a uniform titanium distribution unobtainable with conventional impregnation methods. The lactic acid chelates of titanium have commonly been used as esterification, polymerization, and crosslinking catalysts, and are commercially available from DuPont among the "Tyzor" series of organic titanates. More generally, we may use any organo-titanate chelate. Thus, we employ lactic acid ammonium salt chelate, trialkanolamine chelates or the $\beta$-dicarboxyl chelates, rather than titanium alkoxides, or other more hydrolyzable titanium compounds.

A preferred process for preparation of the catalyst of this invention comprises:

1. Combining one part of an aqueous sodium silicate solution containing about 12% to about 13% $SiO_2$, at a $SiO_2$ to $Na_2O$ weight ratio of about 3.22 with 0.94 parts of a second, clear aqueous solution of an organo-titanate chelate containing 0.18 to 0.32% titanium as $TiO_2$ and wherein the titanium has a coordination number of at least 5, 0.24 to 0.26 gram-equivalents per liter of a tetra-alkyl ammonium halide or hydroxide, up to 0.12 (preferably about 0.06 to about 0.12) gram-equivalents per liter of a magnesium salt, and about 3.3 to about 3.5 gram-equivalents per liter of sodium chloride, to form a gel.
2. Crystallizing the gel formed in (1.) under extended hydrothermal treatment, i.e. 150°-200° C. for 2-6 days at autogenous pressure.
3. Following hydrothermal treatment, the crystalline product is recovered by filtration and washed prior to drying and calcination at 150° C. and 580° C., respectively.

4. The calcined material is treated with an aqueous solution of ammonium salt to remove residual sodium and recalcined to give the desired catalytic form.

The unique feature of this invention is the introduction of a titanium-containing compound directly into the synthate by the vehicle of a hydrolyis resistant chelate, which gives rise to a unique distribution of titania and the resultant useful catalytic properties of this material.

Following are several examples of the preparation of the catalysts of our invention.

In the following examples and description, the trademark Tyzor LA identifies a 50% solution of the ammonium salt of lactic acid titanate chelate in water. The trademark Tyzor TE identifies an 80% solution in isopropanol of triethanolamine titanate chelate.

EXAMPLE I

A solution (I) was made of 185.2 g sodium silicate ("N" brand containing 28.7% $SiO_2$) and 230.2 g deionized water. Another solution (II) was prepared of 311.3 g deionized water, 24.2 g tetrapropyl ammonium bromide, 69.1 g sodium chloride, 9.00 g "Tyzor LA", an ammonia salt of a lactic acid chelate of titanium VI made by DuPont, and 32.36 g $MgCl_2.6H_2O$. The two solutions were mixed well together by adding them simultaneously to a flask and stirring for 15 minutes. The mixture, including the precipitate formed, was placed in a 600 ml Teflon beaker in an autoclave.

The initial temperature set point was 230° C. and was reset at 226 about 19½ hours later and kept there for another 71 hours. Thermocouple measurements in the flask ranged from 180°–182° C. throughout; the pressure ranged from 140–150 psig. The material was dried at 150° C. for three days and calcined at 550° C. for 16 hours. The recovered material had an X-ray diffraction pattern characterized in the following Table I.A.

TABLE I.A.

| X-ray Diffraction Data for Example I | | |
|---|---|---|
| 2θ | d(A) | I/Io × 100 |
| 7.75 | 11.39 | 49 |
| 8.30 | 10.64 | 13 |
| 8.70 | 10.16 | 100 |
| 13.70 | 6.46 | 13 |
| 14.60 | 6.06 | 17 |
| 17.65 | 5.02 | 26 |
| 20.20 | 4.39 | 12 |
| 20.70 | 4.29 | 15 |
| 26.70 | 3.336 | 17 |
| 29.70 | 3.005 | 18 |

The washed and calcined catalysts were examined by scanning electron microscopy (SEM). An Etec SEM, with electron beam control by a Tracor Northern computer, was used to analyze particle-by-particle the microtomed magnesium-titanium-silicon distributions. A 20 kV accelerating voltage was used, and with digital electron beam control an energy dispersive X-ray spectrometer gave accurate elemental compositional data for the individual scan points across a given particle. Sample preparation involved the dispersion of a 15–30 micron powder on a polycarbonate membrane filter. The data is presented as a table (I.B.) of relative composition versus weight distribution of each particle analyzed. The narrow weight distributions observed are indicative of the uniform nature of the catalyst composition described in the following Table I.B.

TABLE I.B.

| SEM Particle-by-Particle Analysis for Example I | |
|---|---|
| | Mass % of Particles |
| % Titanium | |
| 0–2 | 12.6 |
| 2–4 | 59.4 |
| 4–6 | 25.4 |
| 6–8 | 2.6 |
| % Magnesium | |
| 0–2 | 0.9 |
| 2–4 | 0.1 |
| 4–6 | 0.5 |
| 6–8 | 1.6 |
| 8–10 | 0.1 |
| 10–12 | 0.6 |
| 12–14 | 4.1 |
| 14–16 | 17.4 |
| 16–18 | 13.4 |
| 18–20 | 42.7 |
| 20–22 | 10.8 |
| 22–24 | 7.2 |
| 24–26 | 0.6 |

EXAMPLE II

A solution (I) containing 181.56 g sodium silicate ("N" brand) and 223.6 g deionized water was added to a flask simultaneously with a solution of 310.2 g deionized water, 23.03 g tetrapropyl ammonium bromide, 33.6 g $MgCl_2.6H_2O$, 68.21 sodium chloride and 17.8 g "Tyzor LA", mixed and stirred well to disperse the precipitate, and placed in the autoclave in a 600 ml flask.

Initial temperature set point was 230° C.; this was maintained at 230°–232° C. for about 63 hours. Measured temperatures ranged from 178° C. to 180° C., and the pressure was 120–125 psig. The material was dried at 150° C. for 16 hours, and calcined at 580° C. for 16 hours.

The calcined material was subjected to further treatment by a three-step ion exchange procedure with a 5% aqueous ammonium chloride solution at 80°–90° C. for 90 minutes each, and washing to remove residual chloride and drying before calcination at 580° C. for 16 hours.

The X-ray diffraction pattern of this material is shown in Table II.A.

TABLE II.A.

| X-ray Diffraction Data for Example II | | |
|---|---|---|
| 2θ | d(A) | I/Io × 100 |
| 8.0 | 11.04 | 25 |
| 8.95 | 9.87 | 100 |
| 17.9 | 4.95 | 24 |
| 23.15 | 3.84 | 42 |
| 23.40 | 3.79 | 38 |
| 23.80 | 3.73 | 19 |
| 24.05 | 3.69 | 17 |
| 27.00 | 3.299 | 14 |
| 45.65 | 1.986 | 20 |

A mass distribution analysis by SEM/EDX (the method described in connection with Example I) again shows an even distribution of titanium throughout.

TABLE II.B.

| SEM Particle by Particle Analysis for Example II | |
|---|---|
| | Mass % of Particles |
| % Titanium | |
| 0–2 | 5.0 |
| 2–4 | 2.7 |
| 4–6 | 19.3 |
| 6–8 | 50.0 |

TABLE II.B.-continued
SEM Particle by Particle Analysis for Example II

| | Mass % of Particles |
|---|---|
| 8-10 | 17.2 |
| 10-12 | 3.4 |
| 12-14 | 0.8 |
| 14-16 | 0.6 |
| 16-18 | 1.1 |
| % Magnesium | |
| 0-2 | 2.1 |
| 2-4 | 2.9 |
| 4-6 | 0.2 |
| 6-8 | 0.1 |
| 8-10 | 3.4 |
| 10-12 | 3.4 |
| 12-14 | 8.5 |
| 14-16 | 49.7 |
| 16-18 | 8.4 |
| 18-20 | 20.6 |
| 20-22 | 0.5 |
| 22-24 | 0.2 |

TABLE III.B.
SEM Particle by Particle Analysis for Example III

| | Mass % of Particles |
|---|---|
| % Titanium | |
| 0-2 | 27.1 |
| 2-4 | 51.9 |
| 4-6 | 17.0 |
| 6-8 | 3.9 |
| 8-10 | 0.1 |
| % Magnesium | |
| 0-2 | 19.8 |
| 2-4 | 41.9 |
| 4-6 | 27.7 |
| 6-8 | 7.3 |
| 8-10 | 2.8 |
| 10-12 | 0.5 |

The following table recites the ingredients of several similar examples.

EXAMPLES

| | Solution I | | Solution II | | | | |
|---|---|---|---|---|---|---|---|
| Ex. | Na Silicate (g) | DI Water (g) | DI Water (g) | TPABr (g) | MgCl $6H_2O$ (g) | NaCl (g) | Ti cpd (g) |
| IV | 182.76 | 224.80 | 311.53 | 23.75 | 33.76 | 68.63 | 10.89 Tyzor TE |
| V | 180.87 | 223.50 | 310.25 | 23.62 | 33.98 | 68.30 | 35.63 Tyzor LA |
| VI | 183.09 | 223.10 | 308.30 | 23.36 | 17.49 | 68.80 | 22.20 Tyzor TE |
| VII | 181.24 | 224.40 | 310.00 | 22.10 | — | 69.10 | 15.59 Tyzor LA |
| VIII | 181.62 | 225.40 | 310.70 | 22.40 | — | 68.19 | 16.90 Tyzor LA |

EXAMPLE III

A solution of 182.25 g of "N" brand sodium silicate and 235.00 g of deionized water was prepared. A second solution of 23.37 g of tetrapropylammonium bromide, 17.63 g of magnesium chloride hexahydrate, 68.22 g of sodium chloride, 9.49 g Tyzor LA and 308.99 g of deionized water was mixed until clear. Both solutions were added simultaneously to a container, and the resultant slurry was stirred vigorously for 15 minutes. This mixture was placed in an autoclave and allowed to crystallize for 63 hours at 182°–184° C., and autogeneous pressure.

The material was recovered by filtration and washed with deionized water. After drying at 150° C. and calcination for 16 hours at 580° C., the material was subjected to powder X-ray diffraction analysis. This data is presented in Table III.A. Compositional analysis by SEM/EDX is provided in Table III.B.

Further treatment included a three-step ion exchange procedure with a 5% aqueous ammonium chloride solution at 80°–90° C. for 90 minutes each, and washing to remove residual chloride and drying before calcination at 580° C. for 16 hours.

TABLE III.A.
X-ray Diffraction Data for Example III

| 2θ | d(A) | I/Io × 100 |
|---|---|---|
| 7.90 | 11.18 | 31 |
| 8.80 | 10.04 | 20 |
| 20.70 | 4.29 | 17 |
| 21.90 | 4.06 | 100 |
| 23.00 | 3.86 | 22 |
| 23.30 | 3.81 | 16 |
| 23.90 | 3.72 | 12 |
| 35.95 | 2.496 | 22 |

An X-ray diffraction data for Example IV is presented in Table IV.A.

TABLE IV.A.
X-ray Diffraction Data for Example IV

| 2θ | d(A) | I/Io × 100 |
|---|---|---|
| 7.70 | 11.47 | 48 |
| 8.65 | 10.21 | 100 |
| 8.85 | 9.98 | 53 |
| 14.55 | 6.08 | 15 |
| 17.65 | 5.02 | 23 |
| 22.85 | 3.88 | 79 |
| 23.15 | 3.83 | 48 |
| 23.50 | 3.78 | 25 |
| 23.75 | 3.74 | 37 |
| 29.70 | 3.006 | 12 |
| 45.40 | 1.996 | 13 |

We have found that chelates of titanium compounds wherein the titanium has a coordination number of at least 5 are superior to those of less than 5.

In Table V is shown data obtained over a nominal 2.2% $TiO_2$, 10% magnesia-silica catalyst of this invention (made by the process of Example II) for the alkylation of toluene with ethylene. Note that the para-isomer, the more valuable form, is the dominant species and is obtained in concentrations considerably in excess of the equilibrium value. Conditions for the collection of these data were 400° C., atmosphere pressure, vapor phase and WHSV (weight hourly space velocity)=1.0 g feed/g cat/hr.

TABLE V

| | Equilibrium | New Catalyst |
|---|---|---|
| ortho-ethyltoluene | 17% | <1% |
| meta-ethyltoluene | 49% | 43% |
| para-ethyltoluene | 34% | 55% |

Significant activity of this catalyst for the alkylation of benzene with isopropanol, alkylation of phenol with methanol and dehydration of isopropanol to propylene has also been observed.

EXAMPLE IX

A catalyst of this invention was prepared according to Example IV. The ammonium chloride washed and calcined version of this catalyst was tested for its ability to catalyze acid catalyzed hydrocarbon conversion reactions, specifically the vapor phase alkylation of toluene with ethylene at 400° C. and atmospheric pressure. The alkylations were carried out in a microcatalytic activity test reactor which used about 0.5-1.0 gm of powdered catalyst. Reagent grade toluene was vaporized in a stream of nitrogen and mixed with a stream of ethylene, both under mass flow control. This vapor mixture was passed over the catalyst sample in a stainless steel tube, which was submerged in an electrically heated, agitated solder bath. The reactor efflent was condensed in a water cooled coil, and the liquid product was collected over a 6-16 hour period and analyzed by gas chromatography. Off-gas was measured with a wet test meter. At a toluene to ethylene ratio of 2.3:1.0 nitrogen as a carrier, and a feed rate of 1.0 gm toluene/gm catalyst/hour a typical liquid product analysis was:

| | |
|---|---|
| toluene | 54.5% |
| ortho-ethyltoluene | <0.1% |
| meta-ethyltoluene | 17.4% |
| para-ethyltoluene | 27.1% |
| other aromatics (benzene, xylenes, ethylbenzene) | 0.6% |
| heavies and polyalkylates | 0.4% |

EXAMPLE X

A sample of the catalyst prepared and treated as in Example I of this patent was mixed with acetic acid digested Catapal SB alumina, and pressed into 1/16" extrudates. After drying at 150° C., and calcining at 550° C. for six hours, the catalyst had about 10% by weight $Al_2O_3$. The extruded catalyst was placed in a 1" OD stainless steel tube reactor, heated by an electric furnace. A preheat section packed with ceramic saddles was used in the first section of the packed bed. After purging with nitrogen at 300° C. and pressurizing to 150 psig, reagent grade isopropanol was pumped through a vaporizer. This vapor was passed downward over the heated bed. Approximately 43 gms/hour of this feed over 44 gms of catalyst produced a weight hourly space velocity of 0.98 gms feed/gms catalyst/hour. A water cooled condenser was used to recover liquid product over a six to eight hour period, and a wet test meter was used to measure gaseous product rate. After twelve hours of operation, liquid and gaseous samples were analyzed by conventional gas chromatography and are tabulated below. This corresponds to 82.2% conversion of isopropanol, and a 92.2% selectivity to propylene. Catalyst activity remained fairly constant over 3 to 5 days of operation.

| | Liquid | Gas |
|---|---|---|
| propylene | 0.91% | 93.0% |
| di-isopropyl ether | 5.43% | 6.1% |
| isopropanol | 73.35% | — |
| benzene and other aromatics | 0.50% | 0.9% |
| water | 19.8% | — |

EXAMPLE XI

A representative catalyst of this invention prepared according to Example III contained 4.1% magnesium at MgO and 2.8% titnia as $TiO_2$ after washing with 5% $NH_4Cl$ at 80° C., dried and then calcined at 550° C. for 16 hours. Approximately 500 mg of the powdered catalyst was loaded into a ¼" stainless steel tube reactor and placed in an electrically heated solder bath. After purging with nitrogen the system was allowed to stabilize for one hour at 375° C. Phenol and methanol were vaporized separately in 2 streams of nitrogen under mass flow control, and introduced into the tube reactor at a weight hourly space velocity of 0.5 gm of liquid feed (methanol plus phenol) per gram of catalyst per hour, at atmospheric pressure. An on-line gas chromatograph was used to verify feed composition; and a condensed liquid product was collected over a sixteen-hour period and analyzed by capillary GC. The product analysis method employed a derivitization technique which formed the trimethyl silyl ethers of the creosols and phenol. This was done to more readily identify specific creosol and xylenol isomers. Average conversion and selectivity was 14.7% and 66% to 2,6 xylenol, respectively. O-creosol and 2,3,6-trimethylphenol were the major by-products.

All strong-acid catalysts catalyze the same series of reactions varying only in degree of activity and not in kind. There are great similarities among all members of strong-acid catalysts. Mechanistically, the formation or constitution of the strong-acid centers may vary. Fundamentally however all of these types of catalysts can donate protons or accept electrons. This transfer is an attribute of strong-acid catalysts and plays an important part in the reaction mechanisms. The ability to donate protons or accept electrons is related to the amount of Bronsted versus Lewis acidity. Both types of strong-acid sites are believed to contribute to catalytic activity.

As a common mechanism, all strong-acid catalyzed reactions involve a carbonium ion complex as an intermediate. The complex can be formed by the addition of a proton from the catalyst to a free electron pair in the organic substrate. Once the complex is formed it can, dependent upon reaction conditions, undergo changes within itself or with many other molecules to accomplish alkylation, isomerization, cracking, dealkylation, disproportionation, dehydration, oligimerization and polymerization, hydrogen transfer, and cyclization. These types of reactions are typically referred to as "acid catalyzed reactions". Of course a catalyst is always capable of catalyzing a reaction in both directions.

Solid materials such as certain aluminas, silica alumina, certain zeolites and the silica-titania of the instant invention with optional magnesia can be demonstrated to have acidic properties by the usual tests for acids, namely titration or reaction with organic or inorganic bases such as pyridine or ammonia. Using such measures of acidity the activity of the catalysts can be correlated with the measured acidity.

The silica-magnesia-titania catalyst of this invention was tested for acidity by titration with gaseous anhydrous ammonia. The quantity of ammonia adsorbed at room temperature is a measure of the total acidity, all acid sites neutralized. However not all of the acid sites are of equal strength, and the amount of ammonia which remains adsorbed on the surface of the catalyst sample as the temperature of the system is increased is indicative of the relative proportion of strong-acid sites on the surface of the catalyst.

A silica-magnesia-titania catalyst similar to that of Example III was tested for acidity by titration with gaseous anhydrous ammonia. As seen in Table VI the silica-magnesia-titania catalyst exhibits significant ammonia adsorption at room temperature—approximately 1.18 milliequivalents per gram of ion exchanged and calcinec catalyst. This is compared to a commercially utilized silica alumina cracking catalyst manufactured by W. R. Grace, #979, which has found use in a number of acid catalyzed reactions. Based on the ammonia adsorption and desorption data, it is evident that both catalyst samples are strong acids. This demonstrates that the catalyst of this invention has a similar acidity to a commercial silica alumina, which is a known strong acid catalyst.

It is felt that this acidity coupled with the shape selective character gives rise to the unique catalytic performance of our invention.

TABLE VI

|  | W. R. Grace Silica Alumina | | Silica-Magnesia Titania | |
|---|---|---|---|---|
| % Ammonia Adsorbed at Room Temp. | 3.1% | | 2.0% | |
| % of total Ammonia Desorbed at Room Temp. | 42.3% | } 100% | 33.2% | } 100% |
| % of Total Ammonia Desorbed after Heating to 450° C. | 57.7% | | 66.8% | |

We may conduct acid catalyzed reactions in the presence of our catalyst in vapor phase contact at temperatures in the range of about 300°–450° C., pressures of about 1 to about 5 atmospheres, and WHSV (weight of feed per weight of catalyst per hour) of about 0.5–1.5.

In the case of the methylation of phenol, the molar ratio of methanol to phenol may range from about 1 to 10.

We claim:

1. Method of alkylating aromatic hydrocarbon compounds comprising contacting such compounds with a lower alkylene or lower alcohol alkylating agent in the presence of a calcined crystalline titania-silica catalyst having a molar ratio of about 0.015 to 0.04 $TiO_2$:1.0 $SiO_2$ and an X-ray diffraction pattern characterized by peaks as follows:

| $2\theta$ | d(A) | $I/I_o \times 100$ |
|---|---|---|
| 7.75 | 11.39 | 49 |
| 8.30 | 10.64 | 13 |
| 8.70 | 10.16 | 100 |
| 13.70 | 6.46 | 13 | at a temperature of from about 300°–450° C., a pressure of about 1 to about 5 atmospheres and at a rate of feed no greater than about 1.5 grams of feed per gram of catalyst per hour.

2. Method of alkylating hydrocarbon compounds comprising contacting such compounds with a lower alkylene or lower alcohol alkylating agent in the presence of a calcined crystalline titania-magnesia-silica catalyst having molar ratios of 0.015 to 0.04 $TiO_2$ and up to 0.17 MgO, and an X-ray diffraction pattern characterized by peaks as follows:

| $2\theta$ | d(A) | $I/I_o \times 100$ |
|---|---|---|
| 7.75 | 11.39 | 49 |
| 8.30 | 10.64 | 13 |
| 8.70 | 10.16 | 100 |
| 13.70 | 6.46 | 13 | at a temperature of from about 300°–450° C., a pressure of about 1 to about 5 atmospheres and at a rate of feed no greater than about 1.5 grams of feed per gram of catalyst per hour.

3. Method of alkylating aromatic hydrocarbons comprising contacting such hydrocarbons with a lower 1-olefin or lower alcohol alkylating agent in the presence of calcined crystalline titania-magnesia-silica catalyst having the molar ratios 0.015 to 0.04 $TiO_2$ and 0.08 to 0.17 MgO to 1.0 $SiO_2$ and up to 0.17 MgO, and an X-ray diffraction pattern characterized by peaks as follows:

| $2\theta$ | d(A) | $I/I_o \times 100$ |
|---|---|---|
| 7.75 | 11.39 | 49 |
| 8.30 | 10.64 | 13 |
| 8.70 | 10.16 | 100 |
| 13.70 | 6.46 | 13 | a temperature of from about 300°–450° C., a pressure of about 1 to about 5 atmospheres and at a rate of feed no greater than about 1.5 grams of feed per gram of catalyst per hour.

4. Method of ethylating toluene comprising reacting ethylene and toluene under ethylating conditions in the presence of a catalyst made by drying and calcining an aqueous mixture of sodium silicate, magnesium chloride and tetra-alkyl ammonium bromide solutions with a solution of an ammonium salt of a lactic acid chelate of titanium VI, and having the following X-ray peaks:

| $2\theta$ | d(A) | $I/I_o \times 100$ |
|---|---|---|
| 7.75 | 11.39 | 49 |
| 8.30 | 10.64 | 13 |
| 8.70 | 10.16 | 100 |
| 13.70 | 6.46 | 13 | at a temperature of from about 300°–450° C., a pressure of about 1 to about 5 atmospheres and at a rate of feed no greater than about 1.5 grams of feed per gram of catalyst per hour.

* * * * *